United States Patent [19]
Kitagaki et al.

[11] 3,944,664
[45] Mar. 16, 1976

[54] SYNERGISTIC ACARICIDE COMPOSITIONS

[75] Inventors: Tadaharu Kitagaki; Yoshio Takahashi, both of Shizuoka; Kiyoshi Takita, Shimizu, all of Japan

[73] Assignee: Sandoz, Inc., E. Hanover, N.J.

[22] Filed: Dec. 13, 1971

[21] Appl. No.: 207,627

[30] Foreign Application Priority Data
Dec. 29, 1970  Japan................................ 45-130183

[52] U.S. Cl.................................... 424/93; 424/180
[51] Int. Cl.$^2$............................................ A01N 15/00
[58] Field of Search................................ 424/180, 93

[56] References Cited
OTHER PUBLICATIONS
Chemical Abstracts 1, Vol. 69, entry 51173r, 1968.
Chemical Abstracts 2, Vol. 70, entry 10613m, 1969.
Chemical Abstracts 3, Vol. 74, entry 22068h, 1971.
Chemical Abstracts 4, Vol. 74, entry 22100n, 1971.

*Primary Examiner*—Richard L. Huff
*Attorney, Agent, or Firm*—Gerald D. Sharkin; Richard E. Vila

[57] ABSTRACT

A synergistic acaricidal composition comprises as a first ingredient the $\beta$-exotoxin of *Bacillus thuringiensis* or a metal salt thereof and has a second ingredient of one or more of the following chemical acaricides:
 1,1-bis-(p-chlorophenyl) ethanol,
 bis-(p-chlorophenyl) sulfide,
 bis-(p-chlorophenoxy) methane.

The first and second ingredients are used generally in a ratio of about 0.5:1 to 10:1 and may be dispersed in a major portion of an agronomically acceptable carrier.

8 Claims, No Drawings

SYNERGISTIC ACARICIDE COMPOSITIONS

BACKGROUND OF THE INVENTION

Organic chlorophenyl or chlorophenoxy acaricides play a leading role in the eradication of destructive ticks. However, the disadvantages of these materials, such as development of resistant strains and the considerable toxicity of the material have been noticed in recent years. Among the most effective and widely used of these organic chloro acaricides are:

1,1-bis-(p-chlorophenyl) ethanol - (called DMC).
bis-(p-chlorophenyl) sulfide - (called DDDS).
bis-(p-chlorophenoxy) methane - (called Neotran).

*Bacillus thuringiensis*, a spore-forming microorganism with crystalline parasporal bodies, has been employed commercially as a microbial insecticide for the control of insects such as species of the order Lepidoptera and certain flies and mites. *B. thuringiensis* and its use as an insect pathogen is described, inter alia, in C. L. Hannay and P. Fitz-James, "The Protein Crystals of *Bacillus thuringiensis* Berliner", *Can. J. Microb.*, I, 694–710 (1955); A. M. Heimpel, "A Critical Review of *Bacillus thuringiensis* var. *thuringiensis* Berliner and Other Crystalliferous Bacteria", *Ann. Rev. Entomology*, 12, 287–322, (1967). *B. thuringiensis* insecticides are quite specific and are harmless to non-susceptible orders of insects, and relatively safe to animals and man.

"Endotoxin" is used by the art to define the toxicity associated with the water-insoluble crystals. "Exotoxin" denotes the so-called heat-stable, water-soluble fly toxin produced by *Bacillus thuringiensis* var. *thuringiensis* organisms. The water-soluble, heat-stable exotoxin was first reported in 1959 when its toxicity against the larvae of flies was noted. A review of the heat-stable exotoxin is contained in the previously mentioned article by A. M. Heimpel. This article summarizes the activity of the exotoxin (therein referred to as B.t. β-exotoxin) and concludes that exotoxin is effective against insects belonging to some species of the orders "Lepidoptera, Diptera, Hymenoptera, Coleoptera, and Orthoptera." It is also reported that the exotoxin affects insects only at molting or during metamorphosis.

The probable chemical structure of *Bacillus thuringiensis* exotoxin has been elucidated by Bond et al., "A Purification and some Properties of an Insecticidal Exotoxin from *Bacillus thuringiensis* Berliner", R. P. M. Bond, C. B. C. Boyce and S. J. French, *Biochem. J.* (1969), 114, 477–488.

The proposed structure is:

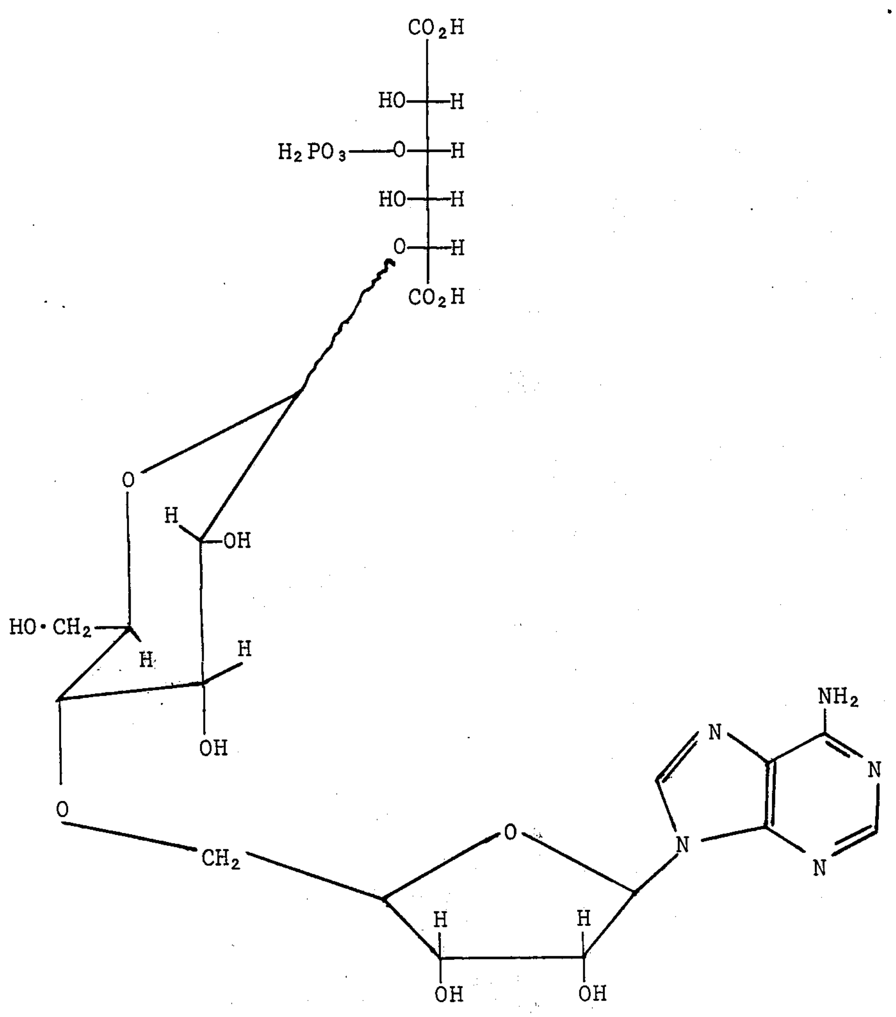

Various processes are known for the production of exotoxin. All involve the fermentation of a *Bacillus thuringiensis* variety *thuringiensis* organism in a medium such as the following:

| Ingredient | Weight (%) |
|---|---|
| Cane Molasses | 0.5 |
| Beet Molasses | 0.5 |
| Cottonseed Oil Meal | 2.0 |
| Casein | 1.0 |
| Corn Steep Liquor | 3.33 |
| $CaCO_3$ | 0.1 |

The medium is adjusted to a pH of about 7.6 with ammonium hydroxide and then sterilized at about 120°C. for about 15 minutes. The medium is inoculated with *Bacillus thuringiensis* var. *thuringiensis* and the fermentation is conducted for about 24 hours at about 30°C. At the termination of the fermentation the cells in the broth are in the pre-spore stage of development and not more than about 1% of the total population contained spores.

The final whole culture is screened through a 200 mesh screen and the resulting mixture of cells and liquor is concentrated at about 125°F. with a vacuum of about 25 inches of mercury. Final drying and micropulverizing produced a 200 mesh powder which is characterized by a $LD_{50}$ of 2.9 mg%.

Another process for the production of both the exotoxin and endotoxin of *Bacillus thuringiensis* is proposed by Drake et al. U.S. Pat. No. 3,087,865. Drake et al. further disclose the precipitation of exotoxin from aqueous supernatant fermentation liquor by addition of calcium chloride. The calcium salt thus produced, as well as corresponding magnesium and barium salts, are disclosed to possess insecticidal activity.

Other salts of β-exotoxin which evidence insecticidal activity and may also be used in accordance with this invention are the copper, cadmium, manganese, tin, zinc, lead, cobalt, aluminum and iron salts.

DESCRIPTION OF THE INVENTION

The present invention proposes to minimize the untoward side effects of certain chloro acaricides and preserve their prominent acaricidal activity. The present invention is based on unexpected findings of marked synergistic activity obtained by the combination of β-exotoxin originated from *Bacillus thuringiensis* with the chloro chemicals, DMC, DDDS, and Neotran. The combination exerts its pesticidal activity at far smaller concentrations as compared with the dosage required in sole applications of the respective ingredients. In addition, the combined composition thus obtained is effective against ticks which have acquired resistance to the aforenamed chloro acaricide.

The said β-exotoxin or the metallic salt thereof provided by the present invention is completely free of living organisms and quite safe to silk worms as well as advantageously being low toxic to the mammal and to the fish.

The present inventors found that β-exotoxin or the metallic salt thereof is effective in certain degree owing to its inhibition on the ecdysis of the larva of ticks. However, it is entirely inactive against the ova and adult insects. In addition, the ecdysis inhibition is lost on the seventh day. Whereas DMC is able to kill the adult insects, its ovacidal effect is quite weak. Likewise, DDDS is able to kill the adult insects, but it is inactive against the larva and ova. Neotran is also active against the adult ticks, but inactive against the ova.

Thus, DMC, DDDS and Neotran to be blended in the present invention possess insecticidal activity against the adult ticks, the activity against the larva and ova being substantially weak, and so they cannot be employed alone. For the eradication of ticks, in addition, the development of drug resistance is rapid, which makes continued use impossible.

The present invention has been achieved based on the finding that blending DMC, DDDS, or Neotran with β-exotoxin endows synergistic insecticidal activity against both adult ticks and the ova or larva thereof with lower dosage, long duration of residual effect, and a smaller tendency to develop drug resistance.

Briefly, the compositions of this invention comprise a first ingredient of the group consisting of β-exotoxin and metal salts thereof and a second ingredient of the group consisting of 1,1-bis-(p-chlorophenyl) ethanol, bis-(p-chlorophenyl) sulfide, bis-(p-chlorophenoxy) methane. The invention also contemplates admixtures of the defined ingredients with an agronomically acceptable carrier, the total active ingredients comprising preferably about 5% to 50% of the admixture of active ingredients and carrier.

Exotoxin is known to possess insecticidal activity against the larvae of the fly. However, the activity is quite weak or nil against most other hazardous insects, and it is practically of no use in eradication of ticks. Nevertheless, blending exotoxin with DMC, DDDS or Neotran results in a composition of high and prolonged activity against ticks.

The dosage and concentration of the acaricidal composition are different depending on the modes of application and field conditions. A typical application would comprise the application of 2000 to 3200 grams per acre of β-exotoxin and 200 to 1600 grams per acre of DMC, DDDS or Neotran. For example, in a 15 year old orange field, spraying 2000 liter per acre of the insecticidal composition comprising 400 ppm of β-exotoxin and 200 ppm of Neotran effects complete eradication of ticks parasiting therein. In the composition of this invention the proportion of exotoxin to organo-chloro acaricide is in the range of 0.5:1 to 10:1, and most preferably 0.5:1 to 2:1.

The acaricidal composition is to be employed by spraying directly or applying after dilution to a suitable concentration in the form of a powder, emulsion, or wettable powder, or upon blending with a carrier and an adjuvant.

The carrier is employed to transport the active ingredient to the desired infected sites, and so it may take the form of a solid, liquid or a gas. For example, the solid carrier may be any of various types of clay, prophyllite, talc, bentonite, white carbon, kaolin, diatomaceous earth, silica or vermiculite, etc.

The liquid carrier may be for example, water, benzene, kerosene, alcohol, acetone, xylene, methyl naphthalene, cyclohexanone, animal and vegetable oils, fatty acids and fatty acid esters.

Ordinary agricultural chemical adjuvants such as spreaders, emulsifiers, caking agents, wet spreaders comprising surfactants exemplified by polyoxyethylene alkylaryl ether, polyvinyl alcohol, polyoxyethylene sorbitanmonothiolate, alkyldimethylbenzylammonium chloride, alkylbenzene sulfonate, may be employed.

The invention is illustrated by the following examples:

EXAMPLE I

The leaves of haricot bean seedlings cultivated in pots 12 cm. in diameter were infested with 50 adult ticks. Subsequently, the leaves were immersed for 10 minutes in dilute solutions of the wettable powders of the acaricides, alone or in combinations thereof prepared according to Example IV-B, and diluted with water to the specified concentrations. The leaves were placed in a sun-room for 2 days and then checked for tick mortality. The results are shown in Table 1.

Table 1

| Insecticides tested | Concentration (ppm) | Insecticidal activity (%) |
| --- | --- | --- |
| β-Exotoxin | 2000 | 25 |
| β-Exotoxin calcium salt | 2000 | 18 |
| β-Exotoxin zinc salt | 2000 | 24 |
| DMC | 25 | 30 |
| DDDS | 250 | 47 |
| Neotran | 500 | 41 |
| β-Exotoxin + DMC | 1000 + 25 | 100 |
| β-Exotoxin + DDDS | 500 + 250 | 93 |
| β-Exotoxin + Neotran | 500 + 500 | 98 |
| β-Exotoxin calcium salt + DMC | 1000 + 25 | 94 |
| β-Exotoxin calcium salt + DDDS | 500 + 250 | 100 |
| β-Exotoxin calcium salt + Neotran | 500 + 500 | 96 |
| β-Exotoxin zinc salt + DDDS | 500 + 250 | 98 |
| β-Exotoxin zinc salt + Neotran | 500 + 500 | 100 |
| Non-treated | — | 0 |

EXAMPLE II

The leaves of haricot bean seedlings cultivated in pots 12 cm. in diameter were infested with 40 to 60 tick ova, and the leaves were immersed for 10 minutes in solutions of wettable powders of various acaricidal compositions diluted with water to specified concentrations. Subsequently the leaves were placed in a sun-room for 10 days and the tick mortality was determined. The results are shown in Table 2.

Table 2

| Insecticides tested | Concentration (ppm) | Insecticidal activity against the ova (%) |
| --- | --- | --- |
| β-Exotoxin | 2000 | 18.6 |
| β-Exotoxin calcium salt | 2000 | 20.0 |
| β-Exotoxin zinc salt | 2000 | 25.4 |
| DMC | 250 | 43.7 |
| DDDS | 1000 | 48.4 |
| Neotran | 1000 | 51.6 |
| β-Exotoxin + DMC | 1000 + 250 | 93.2 |
| β-Exotoxin + DDDS | 1000 + 1000 | 100.0 |
| β-Exotoxin + Neotran | 1000 + 1000 | 100.0 |
| β-Exotoxin calcium salt + DMC | 1000 + 250 | 100.0 |
| β-Exotoxin calcium salt + DDDS | 1000 + 1000 | 100.0 |
| β-Exotoxin calcium salt + Neotran | 1000 + 1000 | 100.0 |
| β-Exotoxin zinc salt + DMC | 1000 + 250 | 100.0 |
| β-Exotoxin zinc salt + DDDS | 1000 + 1000 | 100.0 |
| β-Exotoxin zinc salt + Neotran | 1000 + 1000 | 100.0 |
| Non-treated | — | 0 |

EXAMPLE III

Wettable powders prepared according to Example IV-B and C were diluted to the specified concentrations with water. The diluted suspensions were sprayed in the amount of 2000 ml. per acre with a portable mechanical sprayer onto fully grown orange trees 15 years old. The number of ticks surviving at the specified time after the treatment (per 50 leaves) were determined. The acaricidal activity is shown in Table 3.

Table 3

| Insecticide tested | Concentration (ppm) | Number of ticks before the treatment | Number of surviving ticks after the treatment | | | | | |
| --- | --- | --- | --- | --- | --- | --- | --- | --- |
| | | | 2 days | 5 days | 8 days | 16 days | 25 days | 40 days |
| β-Exotoxin | 1000 | 157 | 81 | 40 | 45 | 48 | 89 | 120 |
| β-Exotoxin calcium salt | 1000 | 164 | 90 | 74 | 38 | 62 | 90 | 140 |
| β-Exotoxin zinc salt | 1000 | 155 | 101 | 101 | 98 | 111 | 120 | 184 |
| DMC | 500 | 111 | 21 | 11 | 1 | 42 | 65 | 102 |
| DDDS | 500 | 156 | 11 | 14 | 18 | 44 | 85 | 113 |
| Neotran | 500 | 130 | 5 | 2 | 5 | 17 | 28 | 69 |
| β-Exotoxin + DMC | 400 + 200 | 142 | 3 | 2 | 1 | 2 | 1 | 10 |
| β-Exotoxin + DDDS | 400 + 200 | 156 | 2 | 9 | 3 | 4 | 4 | 17 |
| β-Exotoxin + Neotran | 400 + 200 | 134 | 2 | 1 | 2 | 1 | 0 | 4 |
| β-Exotoxin calcium salt + DMC | 400 + 200 | 132 | 5 | 3 | 1 | 12 | 14 | 19 |
| β-Exotoxin calcium salt + DDDS | 400 + 200 | 114 | 8 | 9 | 1 | 7 | 11 | 22 |
| β-Exotoxin calcium salt + Neotran | 400 + 200 | 152 | 2 | 1 | 1 | 1 | 4 | 10 |
| β-Exotoxin zinc salt + DMC | 400 + 200 | 162 | 6 | 4 | 2 | 1 | 1 | 8 |
| β-Exotoxin zinc salt + DDDS | 400 + 200 | 148 | 11 | 8 | 6 | 1 | 16 | 29 |
| β-Exotoxin zinc salt + Neotran | 400 + 200 | 112 | 3 | 1 | 1 | 1 | 2 | 13 |
| Non-treated | — | 132 | 83 | 102 | 141 | 286 | 186 | 240 |

The acaricidal composition of this invention can be prepared in the form of dust, wettable powder, emulsion, granule, or aqueous solution by blending the active ingredients with a suitable carrier and, if desired, adding a surfactant, dispersing agent, spreader, or the like.

The present invention is further illustrated in detail by the following examples.

EXAMPLE IV

A. Powders

The mixture comprising by weight 10% β-exotoxin calcium salt (containing 20% free β-exotoxin), 1% DMC, and 89% kaolin is blended and pulverized into a fine powder.

B. Wettable powder

β-Exotoxin (50% content) 40%, DDDS 10%, sodium dodecyl benzene sulfonate 2%, sodium dinaphthyl methane disulfonate 2%, (all by weight) are blended and pulverized with 46% of a 50/50 mixture of diatomaceous earth and clay. The resulting mixture provides a satisfactory wettable powder.

C. Wettable powder

Zinc salt of β-exotoxin (containing 20% of β-exotoxin) 50%, neotran 5%, sodium dodecyl sulfate 2%, sodium lignin sulfonate 3% (all by weight) are blended and pulverized with a 50/50 mixture of diatomaceous earth and clay. The resulting mixture is a satisfactory wettable powder.

D. Emulsion

β-Exotoxin 10%, Neotran 10%, DMSO (dimethyl sulfoxide) 30%, cyclohexanone 30%, and sorbol 20%, are mixed to provide a concentrate satisfactory for the preparation of aqueous emulsions on addition of water.

What is claimed is:

1. An acaricidal composition consisting essentially of a first ingredient of the group consisting of β-exotoxin and metal salts thereof and a second ingredient of the group consisting of 1,1-bis-(p-chlorophenyl) ethanol, bis-(p-chlorophenyl) sulfide and bis-(p-chlorophenoxy) methane; said first and second ingredients being present in the ratio of about 0.5:1 to about 10:1 by weight.

2. A composition of claim 1 in which said second ingredient is 1,1-bis-(p-chlorophenyl) ethanol; and said first and second ingredients are present in the ratio of about 0.5:1.0 to about 2.0:1.0.

3. A composition of claim 1 in which said second ingredient is bis-(p-chlorophenyl) sulfide; and said first and second ingredients are present in the ratio of about 0.5:1.0 to about 2.0:1.0.

4. A composition of claim 1 in which said second ingredient is bis-(p-chlorophenoxy) methane; and said first and second ingredients are present in the ratio of about 0.5:1.0 to about 2.0:1.0.

5. An insecticidal composition comprising a major portion of an agronomically acceptable carrier and about 5% to about 50%, based upon the weight of said composition, of active ingredients consisting essentially of a first ingredient of the group consisting of β-exotoxin and metal salts thereof and a second ingredient of the group consisting of 1,1-bis-(p-chlorophenyl) ethanol, bis-(p-chlorophenyl) sulfide, and bis-(p-chlorophenoxy) methane; said first and second ingredients are present in the ratio of about 0.5:1.0 to about 10.0:1.0.

6. A composition of claim 5 in which said second ingredient is 1,1-bis-(p-chlorophenyl) ethanol; said first and second ingredients are present in the ratio of about 0.5:1.0 to about 2.0:1.0.

7. A composition of claim 5 in which said second ingredient is bis-(p-chlorophenyl) sulfide; said first and second ingredients are present in the ratio of about 0.5:1.0 to about 2.0:1.0.

8. A composition of claim 5 in which said second ingredient is bis-(p-chlorophenoxy) methane; said first and second ingredients are present in the ratio of about 0.5:1.0 to about 2.0:1.0.

* * * * *